United States Patent
Wu et al.

(10) Patent No.: US 8,198,463 B2
(45) Date of Patent: Jun. 12, 2012

(54) PROCESS FOR THE PREPARATION OF 6,6-DIMETHYL-3-AZABICYCLO-[3.3.0]-HEXANE COMPOUNDS AND ENANTIOMERIC SALTS THEREOF

(75) Inventors: George Wu, Basking Ridge, NJ (US); Frank X. Chen, Plainsboro, NJ (US); Paitoon Rashatasakhon, Samutsakhon (TH); Jeffrey M. Eckert, Hazlet, NJ (US); George S. K. Wong, Summit, NJ (US); Hong-Chang Lee, Livingston, NJ (US); Nolan C. Erickson, West Orange, NJ (US); Jennifer Ann Vance, Scotch Plains, NJ (US); Peter C. Nirchio, Lebanon, NJ (US); Juergen Weber, East Windsor, NJ (US); David Jieh-Shyh Tsai, Warren, NJ (US); Nanfei Zou, East Brunswick, NJ (US)

(73) Assignee: Schering Corporation, Kenilworth, NJ (US)

( * ) Notice: Subject to any disclaimer, the term of this patent is extended or adjusted under 35 U.S.C. 154(b) by 186 days.

(21) Appl. No.: 12/757,322

(22) Filed: Apr. 9, 2010

(65) Prior Publication Data
US 2010/0256393 A1   Oct. 7, 2010

Related U.S. Application Data

(62) Division of application No. 11/792,770, filed as application No. PCT/US2006/048613 on Dec. 20, 2006, now Pat. No. 7,723,531.

(60) Provisional application No. 60/753,215, filed on Dec. 22, 2005.

(51) Int. Cl.
*C07D 209/52*   (2006.01)
(52) U.S. Cl. ......... 548/515; 548/452
(58) Field of Classification Search .......... 548/452, 548/515
See application file for complete search history.

(56) References Cited

U.S. PATENT DOCUMENTS

| 4,183,857 | A |   | 1/1980 | Kollmeyer |          |
|-----------|---|---|--------|-----------|----------|
| 4,659,838 | A |   | 4/1987 | Lerch     |          |
| 4,691,022 | A |   | 9/1987 | Henning et al. |    |
| 6,992,220 | B2 |  | 1/2006 | Chen et al. |        |
| 7,012,066 | B2 |  | 3/2006 | Sakena et al. |      |
| 7,244,721 | B2 |  | 7/2007 | Sakena et al. |      |
| 7,309,717 | B2 |  | 12/2007 | Park et al. |       |
| 7,326,795 | B2 |  | 2/2008 | Sudhakar et al. |    |
| 7,528,263 | B2 |  | 5/2009 | Wu et al. |          |
| 7,569,705 | B2 | * | 8/2009 | Park et al. | 548/515 |
| 7,592,316 | B2 |  | 9/2009 | Njoroge et al. |     |
| 7,595,419 | B2 |  | 9/2009 | Chen et al. |        |
| 7,723,531 | B2 | * | 5/2010 | Wu et al. | 548/515 |
| 7,728,165 | B2 | * | 6/2010 | Park et al. | 560/124 |

FOREIGN PATENT DOCUMENTS

| CA | 1 117 128 | 1/1982 |
| EP | 0010799 | 10/1979 |
| EP | 0 010 799 B1 | 5/1982 |
| JP | 60-146871 | 8/1985 |
| WO | WO2004/113295 A1 | 12/2004 |

OTHER PUBLICATIONS

Mukaiyama, et al., "An asymmetric synthesis of bicyclic lactones and its application to the asymmetric synthesis of (1R, 3S)-cis-chrysanthemic acid" Chemistry Letters, 1983, No. 3, pp. 385-388.

* cited by examiner

*Primary Examiner* — Golam M M Shameem
(74) *Attorney, Agent, or Firm* — Julie M. Lake; Sheldon O. Heber

(57) ABSTRACT

The present invention provides for a process for preparing racemic methyl 6,6-dimethyl-3-azabicyclo[3,1,0]hexane-2-carboxylate, its corresponding salt: (1R,2S,5S)-methyl 6,6-dimethyl-3-azabicyclo[3,1,0]hexane-2-carboxylate di-p-toluoyl-D-tartaric acid ("D-DTTA") salt or a (1S,2R,5R)-methyl 6,6-dimethyl-3-azabicyclo[3,1,0]hexane-2-carboxylate di-p-toluoyl-L-tartaric acid salt ("L-DTTA") in a high enantiomeric excess. This invention also provides for a process for preparing a (1R,2S,5S)-methyl 6,6-dimethyl-3-azabicyclo[3,1,0]hexane-2-carboxylate dibenzoyl-D-tartaric acid ("D-DBTA") salt or a (1S,2R,5R)-methyl 6,6-dimethyl-3-azabicyclo[3,1,0]hexane-2-carboxylate L-tartaric acid ("L-DBTA") salt in a high enantiomeric excess. Further, this invention provides a process for preparing intermediates II, IIB, III, IV, IV salt, V, VI, and VII.

3 Claims, No Drawings

PROCESS FOR THE PREPARATION OF 6,6-DIMETHYL-3-AZABICYCLO-[3.3.0]-HEXANE COMPOUNDS AND ENANTIOMERIC SALTS THEREOF

CROSS-REFERENCE TO RELATED APPLICATIONS

This patent application is a divisional application based on and claiming the priority of U.S. patent application Ser. No. 11/792,770, filed Jun. 8, 2007, now allowed, which application in turn is based on and claims the priority of PCT Patent Application No. PCT/US2006/048613, filed Dec. 20, 2006, which in turn is based on and claims the priority of U.S. Provisional Patent Application Ser. No. 60/753,215, filed Dec. 22, 2005, each of which prior applications are incorporated by reference as if fully set forth herein.

FIELD OF THE INVENTION

The present invention relates to a process for preparing racemic methyl 6,6-dimethyl-3-azabicyclo[3.1.0]hexane-2-carboxylate (free base) and a process for providing corresponding salts, (1R,2S,5S)-methyl 6,6-dimethyl-3-azabicyclo-[3.1.0]hexane-2-carboxylate di-p-toluoyl-D-tartaric acid ("D-DTTA" salt) and (1R,2S,5S)-methyl 6,6-dimethyl-3-azabicyclo[3.1.0]hexane-2-carboxylate dibenzoyl-D-tartaric acid ("D-DBTA") salt in a high enantiomeric excess. This invention also relates for a process for precipitating from a solution of the racemic methyl 6,6-dimethyl-3-azabicyclo [3.1.0]hexane-2-carboxylate the corresponding (1S,2R,5R)-methyl 6,6-dimethyl-3-azabicyclo[3.1.0]hexane-2-carboxylate di-p-toluoyl-L-tartaric acid salt ("L-DTTA" salt) and (1S,2R,5R)-methyl 6,6-dimethyl-3-azabicyclo[3.1.0]hexane-2-carboxylate L-tartaric acid ("L-DBTA" salt) with high enantiomeric specificity, leaving a high enantiomeric excess of the corresponding (1R,2S,5S)-methyl 6,6-dimethyl-3-azabicyclo-[3.1.0]hexane-2-carboxylate free base in solution. Further, this invention relates a process for preparing intermediates II, IIB, III, IV, IVB, V, VI, and VII.

The compounds obtained by these processes are useful as intermediates in the synthesis of compound that have, for example, medicinal value.

BACKGROUND OF THE INVENTION

Identification of any publication in this section or any section of this application is not an admission that such publication is prior art to the present invention.

Esters of 6,6-dimethyl-3-azabicyclo[3.1.0]hexane-2-carboxylic acid are useful as intermediates in the synthesis of compounds that have utility, for example, as pharmaceuticals. For example, (1R,2S,5S)-6,6-dimethyl-3-azabicyclo[3.1.0]-hexane-2-carboxylic acid, methyl ester hydrochloride is disclosed in US Publication No. 2003-0216325 A1 which is incorporated herein by reference. This compound is a key intermediate used in preparation of the hepatitis C virus ("HCV") protease inhibitor having the following structure of formula Z:

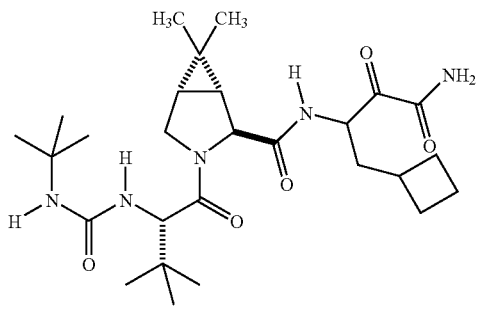

The compound of formula Z is useful for treating hepatitis C and related disorders. Specifically, the compound of formula Z is an inhibitor of the HCV NS3/NS4a serine protease.

Various methods are known in the art to make esters of 6,6-dimethyl-3-azabicyclo[3.1.0]hexane-2-carboxylic acid, which have the formula

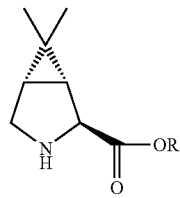

where R is, for example, alkyl, aryl, aralkyl, cycloalkyl and cycloalkylalkyl.

For example, US Publication No. 2003-0216325 A1 discloses preparation of compound 1

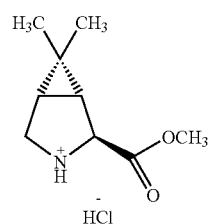

from the corresponding alcohol 2

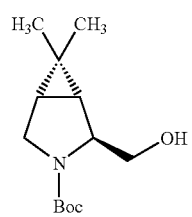

by performing a Jones oxidation and then cleaving the protection with methanolic HCl. This procedure modifies the one disclosed by R. Zhang and J. S. Madalengoitia in *J. Org. Chem.*, 64, pp 330-31 (1999).

US Publication No. US 2005/0020689 A1, herein incorporated by reference, discloses a process for making 3-(amino)-3-cyclobutyl methyl-2-hydroxy-propionamide or a salt thereof, which is an intermediate in the synthesis of compound Z. This publication also claims some intermediates prepared in the synthesis.

US Publication No. US 2005/0059800, herein incorporated by reference, claims an alternative process for preparing the compound of formula Z, which involves using methyl 6,6-dimethyl-3-azabicyclo[3.1.0]hexane-2-carboxylic acid as a starting material.

US Publication No. US 2005/0059684 A1, herein incorporated by reference, prepares esters of 6,6-dimethyl-3-azabicyclo[3.1.0]hexane-2-carboxylic acid in a process summarized by Scheme 1 derivative is prepared by direct oxidation of a bicyclo-pyrrolidine compound of the formula

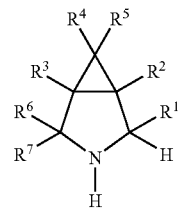

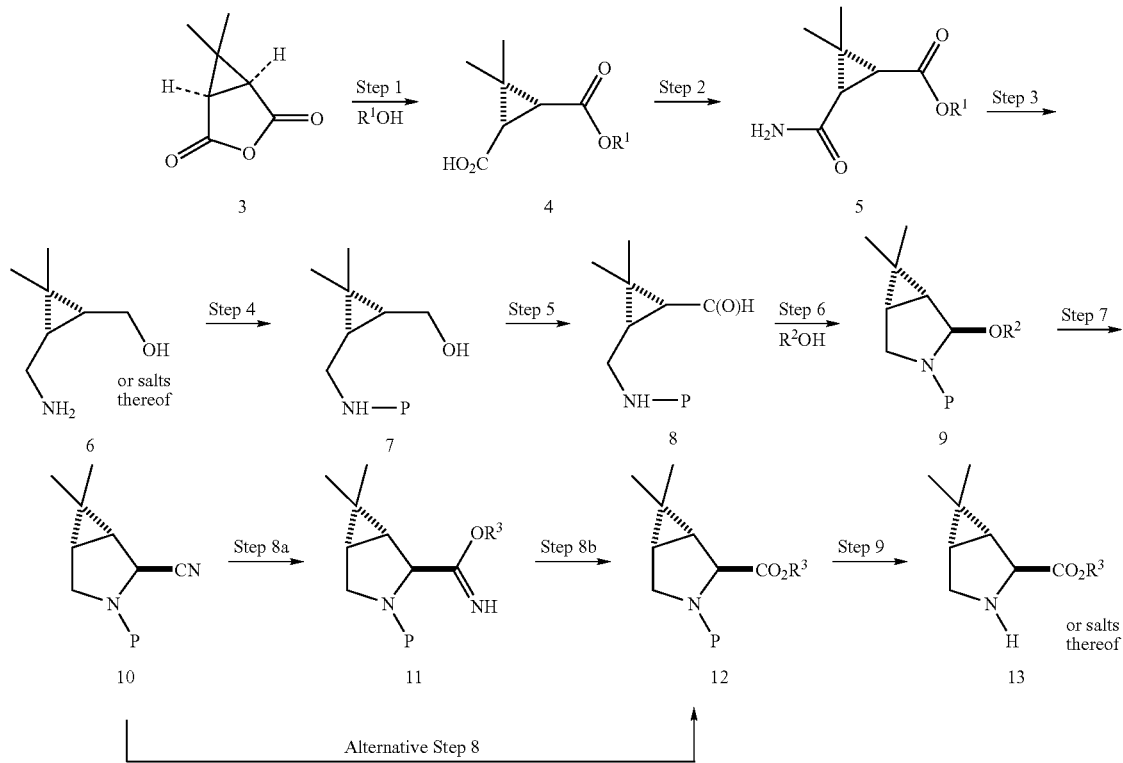

Scheme 1

EP 0 010 799 (the '799 publication) discloses a process for preparing acid compounds of the formula

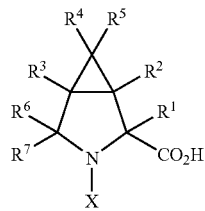

where $R^1$ is hydrogen or alkyl and $R^2$ to $R^7$ are, for example, alkyl, from the corresponding imine through a nitrile intermediate. Accordingly, the imine is reacted with a cyanating reagent to form the corresponding nitrile, which is subsequently hydrolyzed to form the acid derivative. The imine or by dehydrohalogenation of the corresponding halo-pyrrolidine derivative of the bicycle-pyrrolidine. The document indicates that the cyanation step forming the nitrile generally leads exclusively to the formation of the trans geometric isomer and this stereochemistry is retained in the hydrolysis step.

U.S. Pat. No. 4,691,022 discloses a process for preparing an acid or ester derivatives of the formula

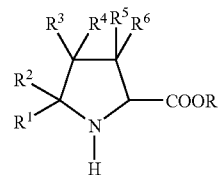

where R is hydrogen or alkyl and R⁴ and R⁵, for example, may form a bicyclic ring system, from the corresponding nitrile. The process comprises converting, with an oxidizing agent in the presence of a silver salt, a pyrrolidine derivative into the corresponding Δ¹-pyrrolidine derivative and subsequently reacting the pyrrolidine derivative with HCN, preferably generated by adding a metal cyanide in the presence of mineral acid to the reaction mixture, to form the nitrile. The product is prepared by subjecting the resulting nitrile to solvolysis. The patent does not disclose a process for making a particular isomer of these compounds in a high enantiomeric excess.

None of these foregoing processes provide one particular enantiomer of the bicyclo-pyrrolidine compound in high enantiomeric purity. Accordingly, there remains a need for methods of providing intermediates useful in the synthesis of compounds useful in the treatment or prevention or amelioration of one or more symptoms of hepatitis C. Further, there remains a need for processes providing enantiomeric intermediates which have a prevalence of the desired enantiomer without resorting to arduous enantiomer separation techniques, for example, chiral chromatography.

In view of the importance of hepatitis C virus ("HCV") protease inhibitors, new, novel methods of making such antagonists are always of interest.

SUMMARY OF THE INVENTION

These and other needs are met by the present invention, which in one aspect provides a process of selectively making a (1R,2S,5S)-I di-p-toluoyl-D-tartaric acid salt (D-DTTA salt) or a (1S,2R,5R)-I di-p-toluoyl-L-tartaric acid salt (L-DTTA salt) from a mixture of compounds of the formulae I and Ia

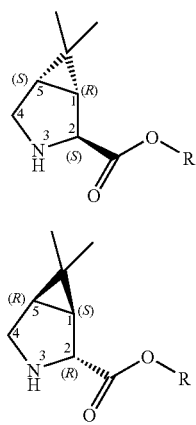

where R is alkyl, substituted alkyl, aryl, substituted aryl, aralkyl, substituted aralkyl, cycloalkyl or substituted cycloalkyl, the process providing an enantiomeric excess of at least 90% of the selected salt by resolution of the racemic mixture with the above acids.

In another aspect, the present invention provides a process for preparing a (1R,2S,5S)-I dibenzoyl-D-tartaric acid salt (D-DBTA salt) or a (1S,2R,5R)-I dibenzoyl-L-tartaric acid salt (L-DBTA salt) from a mixture of compounds of the formulae I and Ia:

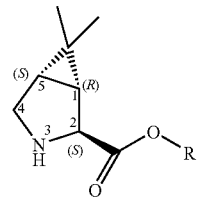

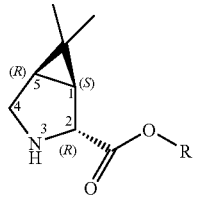

where R is alkyl, substituted alkyl, aryl, substituted aryl, aralkyl substituted aralkyl, cycloalkyl, or substituted cycloalkyl, the process providing the selected salt an enantiomeric excess of at least 85% by resolution of the racemic mixture with the above acids.

Another aspect of the present invention provides acid salt compounds of formulae IA and IaA:

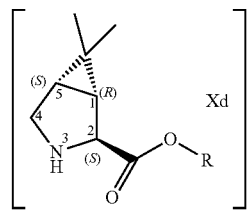

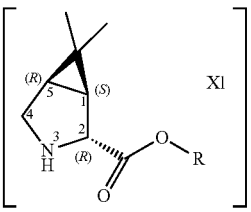

wherein
R represents an alkyl, substituted alkyl, aryl, substituted aryl, aralkyl substituted aralkyl, cycloalkyl, or substituted cycloalkyl group, preferably wherein R is $C_1$-$C_8$ alkyl, more preferably, R is methyl; "Xd" is selected from D-DTTA and D-DBTA, and "Xl" is selected from L-DTTA and L-DBTA.

Another aspect of the present invention provides a process for the provision of intermediates of formula IIB and the intermediates of formula IIB:

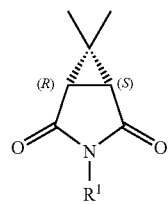

wherein R¹ is aralkyl, substituted aralkyl or alkenyl, preferably R¹ is selected from benzyl and allyl.

Another aspect of the present invention is a process for the provision of intermediates of formula IVB and the provision of intermediates of formula IVB:

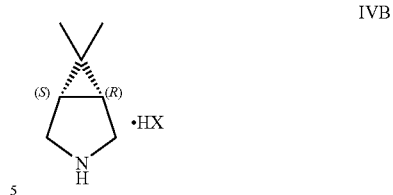

IVB wherein X is an anion, preferably, Cl, Br, I, $NO_3$, or $HSO_4$.

Another aspect of the present invention is the provision of D-DTTA and D-DBTA salts of formula I and the provision of L-DTTA and L-DBTA salts of formula Ia in high yield from a mixture of the compounds of formula I and Ia, and the process of providing one stereoisomer in a high enantiomeric excess from the mixture.

DESCRIPTION OF THE INVENTION

As used above, and throughout the specification, the following terms, unless otherwise indicated, shall be understood to have the following meanings:

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)₂, carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl, groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, and alkoxy. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent, such as those defined above. Suitable, non-limiting examples include: H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups is as previously described. Non-limiting examples of suitable aralkyloxy groups include benzyloxy and 1- or 2-naphthalenemethoxy. The bond to the parent moiety is through the ether oxygen.

"Alkylamino" means an —NH$_2$ or —NH$_3^+$ group in which one or more of the hydrogen atoms on the nitrogen is replaced by an alkyl group as defined above.

"Arylamino" means an —NH$_2$ or —NH$_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O$_2$)— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

Enantiomeric excess ("e.e.") is a percentage expressing the extent to which one enantiomer (e.g., R-enantiomer) is produced over the other (e.g. S-enantiomer), calculated by subtracting the difference in the amount of each enantiomer produced divided by the sum of the amount of each enantiomer produced.

In one embodiment, the present invention provides a process for preparing in enantiomeric excess a D-DTTA or a D-DBTA salt of the compound of formula I from a racemic mixture. In another embodiment, the present invention provides a process for preparing in enantiomeric excess an L-DTTA or an L-DBTA salt of a compound of formula Ia from a racemic mixture. The inventive process is described in Scheme I below:

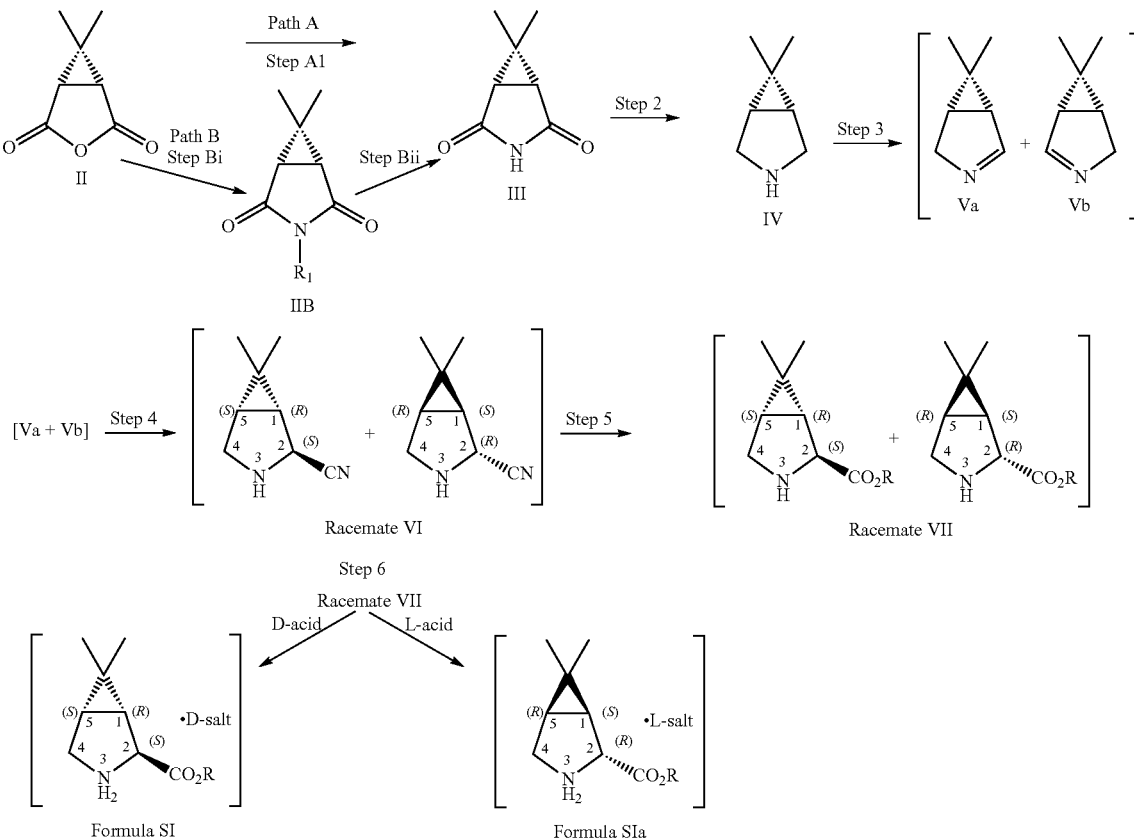

wherein

R is an alkyl, substituted alkyl, aryl, substituted aryl, aralkyl substituted aralkyl, cycloalkyl, or substituted cycloalkyl group. Non-limiting examples of alkyl groups are $(C_1-C_{12})$ alkyl, $(C_1-C_8)$alkyl and $(C_1-C_3)$alkyl. $R^1$ is an aralkyl, substituted aralkyl or alkenyl (e.g., allyl) groups; D-acid is selected from di-p-toluoyl-D-tartaric acid (D-DTTA) and dibenzoyl-D-tartaric acid (D-DBTA); D-salt is the anion corresponding to the D-acid selected, that is, either di-p-toluoyl-D-tartarate or dibenzoyl-D-tartarate; L-acid is selected from di-p-toluoyl-L-tartaric acid (L-DTTA) and dibenzoyl-L-tartaric acid (L-DBTA); and L-salt is the anion corresponding to the L-acid selected, that is, either di-p-toluoyl-L-tartarate or dibenzoyl-L-tartarate.

In some embodiments where the (1S,2R,5R) enantiomer is not the desired enantiomer, it is preferred to carry out Step 6 by precipitating the less desirable (1S,2R,5R) enantiomer from solution with the L-acid (e.g. precipitate the compound of formula SIa), whereupon the filtrate containing the more desirable (1R,2S, 5S) enantiomer (e.g. the compound of formula SI) is subsequently worked up to obtain the more desirable enantiomer in improved enantiomeric excess. In these embodiments the workup of the filtrate can optionally include a second precipitation of the desired (1R,2S,5S) enantiomer from the filtrate by treatment of the filtrate with the selected D-acid, as described below in detail for step 6, or merely evaporating off the solvent to provide a solid.

There follows a detailed discussion of each of the steps of the process represented in Scheme I.

Step 1—Imide Formation

A precursor imide is formed from caronic acid (IIa) starting material following one of two procedures, procedure A, which forms the imide in one step, and procedure B, which forms the imide in two steps using different reactants. Methods to prepare caronic anhydride are known in the art and this compound may be made, for example, from the synthesis disclosed in US Publication No. 2005/0059648 A1, which in Example 1 therein details a method for preparing the anhydride from ethyl chrysanthemumate in accordance with published procedures.

An alternate procedure, shown in Scheme II, may be used to provide the starting material, which can be isolated, or used in situ to form the compound of formula III.

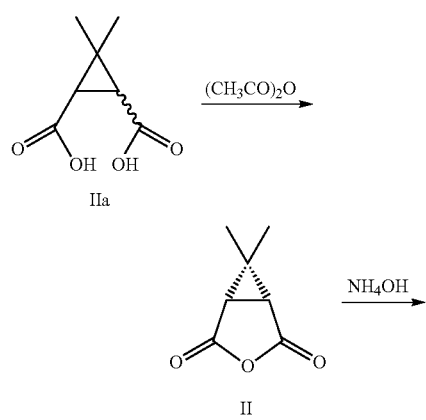

Scheme II

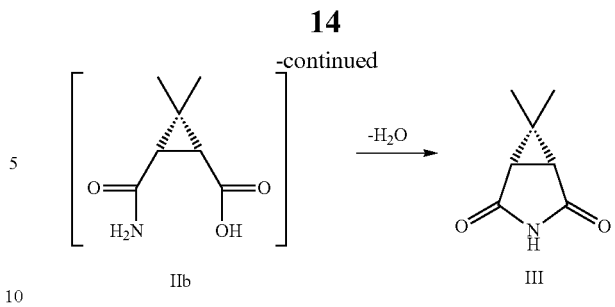

As shown in Scheme II, racemic 3,3 dimethyl-cyclopropane-1,2-dicarboxylic acid (IIa) is dissolved/suspended in toluene and treated with acetic anhydride in the presence of sulfuric acid to form cis-caronic anhydride preferentially (formula II). The cis-caronic anhydride may be isolated for use. Alternatively, the resulting reaction mixture containing cis-caronic anhydride is treated with ammonium hydroxide forming the ring-opened intermediate and heated in situ to form, in a one-pot reaction, the imide of formula III.

Procedure A:

Caronic anhydride (formula II) can be catalytically converted to the compound of formula III in a suitable solvent to yield the imide of formula III. In some embodiments of the invention it is preferred to employ solvents selected from water, tetrahydrofuran, methanol, isopropanol, methyl isobutyl ketone, xylenes, and formamide. Suitable catalysts for carrying out this conversion include, for example, 4-N,N-dimethylaminopyridine (DMAP) and lutidine. The catalyst is employed in the presence of a nitrogen source. Suitable nitrogen source reagents include, but are not limited to, $NH_3$, $NH_4OH$, $H_2NC(O)NH_2$, $H_2NC(O)H$, $NH_4O_2CH$, and $NH_4O_2CCH_3$. In some embodiments it is preferred to carry out the reaction at a temperature of from about 10° C. to about 200° C.

Procedure B (Two Steps):

A second method for the provision of the compound of formula III from caronic anhydride (formula II) is a two-step sequence to yield the imide of formula III.

Step Bi:

An intermediate alkylimide of formula IIB is prepared from caronic anhydride by reaction with a reagent selected from an aralkyl, substituted aralkyl or alkenyl amine in the presence of a solvent. In some embodiments of the invention it is preferred to employ amines selected from $ArylCH_2NH_2$ and $AllylNH_2$. In some embodiments of the invention it is preferred to use a solvent selected from t-butyl methylether (TBME), tetrahydrofuran, methanol, toluene, xylene and mixtures of two or more thereof. In some embodiments of the invention it is preferred to carry out the reaction at a temperature of from about 0° C. to about 200° C.

Step Bii:

The intermediate alkylimide of formula IIB can be converted to compound III by hydrogenating the intermediate using metal-mediated hydrogenolysis reaction conditions. In some embodiments it is preferred to use a catalyst comprising palladium on carbon (Pd/C) in the presence of hydrogen gas. One example of suitable reaction conditions can be found in the following reference: R. C. Bernotas and R. V. Cube, *Synthetic Communication*, 1990, 20, 1209.

Step 2

The imide ring in the bicyclo-compound of formula III is converted to a pyrrolidine ring to yield the bicyclo-compound of formula IV by reduction in a suitable solvent. In some embodiments it is preferred to carry out this reduction using a reagent selected from lithium aluminum hydride ("LiAlH$_4$"), sodium bis(2-methoxyethoxy)aluminum dihydride ("RED-AL®"), and borane. In some embodiments of the invention it is preferred to carry out the reduction reaction in a solvent selected from tetrahydrofuran, 2-methyl tetrahydrofuran, tert-butyl methyl ether, 1,2-dimethoxyethane, toluene and mixtures of two or more thereof. In some embodiments it is preferred to isolate the product by distilling off the solvent. In some embodiments of the invention it is preferred to carry out the reduction reaction at a temperature of from about −20° C. to about 80° C.

Optionally, the compound of formula IV may be converted to the corresponding salt (compound of formula IVB) by reacting it with an acid. Suitable acids include, but are not limited to, mineral acids, for example, HCl, HBr, HI, HNO$_3$ or H$_2$SO$_4$. In some embodiments it is preferred to use a suitable organic solvent to provide a mineral acid solution for this treatment, for example, alcohol solvents, for example methanol and isopropanol.

Step 3:

The pyrrolidine ring in the bicyclo-compound compound of formula IV is oxidized to yield the corresponding imine. Since the multiple bond introduced into the pyrrolidine ring can be introduced in either of two locations on the ring, this step yields a mixture of isomer compounds of formulae Va and Vb.

In some embodiments it is preferred to carry out the oxidation by treating the compound of formula IV with an oxidation reagent selected from ammonium, alkali metal or alkaline earth metal peroxodisulfates, more preferably sodium or potassium peroxodisulfate and a catalytic amount of a silver catalyst, preferably from about 0.01 to about 0.10 molar equivalents of a silver salt catalyst for example silver nitrate. In these embodiments it preferred to use a solvent comprising water or a water/solvent mixture, for example water mixed with a solvent selected from acetonitrile and mixtures thereof. In some embodiments it is preferred to select the oxidizing reagent from manganese(IV) dioxide in hydrocarbon or ethereal solvents, (e.g., hexanes, n-heptane, and tert-butyl methyl ether). In some embodiments it is preferred to use a peroxide selected from urea hydrogen peroxide and hydrogen peroxide in a water/solvent mixture. In some embodiments using a peroxide it is preferred to select the solvent for the water/solvent mixture from acetonitrile, ethylacetate, isopropylacetate, tertiary-butyl methyl ether (TBME), hexanes, tetrahydrofuran and 2-methyl-tetrahydrofuran and mixtures of two or more thereof, catalyzed by 0.001 to 0.10 molar equivalents of manganese(III) salts, e.g., (1R,2R)-(−)-[1,2-cyclohexanediamino-N,N'-bis(3,5-di-tert-butylsalicylidene)]-manganese(III) chloride ([R,R-Salen]Mn$^{III}$Cl), (1S,2S)-(+)-[1,2-cyclohexanediamino-N,N'-bis(3,5-di-tert-butylsalicylidene)]manganese(III) chloride, ([S,S-Salen] Mn$^{III}$Cl), and copper salts, for example, copper acetate and optionally tetramethylethylenediamine. In some embodiments it is preferred to use iodosobenzene (PhIO) in chlorinated solvents, (e.g., dichloromethane or 1,2-dichlorobenzene).

In some embodiments, it is preferred to employ potassium peroxodisulfate with silver nitrate in the presence of an alkali-metal cyanide, preferably potassium cyanide. In some embodiments utilizing this oxidation method, it is preferred to employ water as the reaction medium and suspend the pyrrolidine substrate undergoing oxidation therein. In some embodiments using potassium peroxodisulfate/silver nitrate oxidation in Step 3, it is preferred to employ a catalytic amount of silver nitrate, for example from about 2 mole % to about 10 mole %, more preferably from about 5 to about 7.5 mole % compared to the amount of substrate present. In some embodiments, it is preferred to employ at least about 1.1 equivalent of potassium peroxodisulfate based on the amount of pyrrolidine substrate to be oxidized along with from about 2.3 equivalents to about 3.0 equivalents of sodium hydroxide dissolved in about 10 volumes to about 15 volumes water. In some embodiments employing the peroxodisulfate/silver nitrate oxidation procedure, it is preferred to use at least 2 equivalents of an alkali metal cyanide, preferably potassium cyanide, in the reaction mixture. In some embodiments employing peroxodisulfate oxidation in Step 3, it is preferred to carry out the reaction at a temperature of from about −5° C. to about +5° C., more preferably from about −5° C. to about 0° C. In some embodiments using potassium peroxodisulfate oxidation in Step 3, it is preferred to work up the reaction by quenching with sodium thiosulfate aqueous solution and extract the product into methyl tertiary butyl ether (MTBE), concentrate the extract and replace the MTBE with methanol by adding methanol to the solution and distilling off the MTBE. In some embodiments utilizing this work up, it is preferred to employ the methanolic solution of the product imine provided by the work up directly in subsequent steps of the inventive process.

Step 4—Cyano-Group Functionalization of Imine and Step 5—Hydrolysis of Cyano-Group:

In Step 4, the imine ring of the bicyclo compound racemate comprising the isomers of formula Va and Vb (also termed herein as the compounds of formula V) is functionalized with a cyano functional group. The addition of the cyano group occurs at carbon 2, with preferential attack on the opposite face of the imine ring from which the methylene group forming the cyclopropyl ring of the bicyclo compound projects. Accordingly, the addition of cyano-group preferentially forms one of the two enantiomers, with reference to Scheme I, shown in brackets as racemate VI. The functionalization is carried out using is carried out in the presence of a cyanating agent, for example, hydrocyanic acid gas (HCN) or is generated in situ using an alkali metal, alkaline earth metal, or transition metal cyanide, preferably sodium or potassium cyanide, and trimethysilyl cyanide ("TMSCN") in the presence of a mineral acid. In some embodiments it is preferred to add the cyanating agent to a suspension of the compounds of formula V in the presence of a protic polar solvent, preferably methanol or a mixture of methanol ("MeOH") and tert-butyl methyl ether ("TBME"). In some embodiments using this methodology it is preferred to render the solvent acidic with the addition of an acid selected from a mineral acid, for example, hydrochloric acid, hydrobromic acid and sulfuric acid, and an organic acid, for example, acetic acid and formic acid. In some embodiments it is preferred to run the reaction with the reaction mixture at a temperature of from about −10° C. to about +120° C., preferably 0° C. In some embodiments it is preferred to use an amount of the cyanating reagent of from about 1.0 to about 1.5 molar equivalents based on the total amount of the compounds of formula V employed.

In some embodiments, following the cyanic acid addition, and without isolating the product, a solvolysis is performed on the cyanated racemate product, with reference to Scheme I, step 5, hydrolysis of racemate VI to yield racemate VII. In some embodiments it is preferred to carry out the hydrolysis with ROH, wherein R, defined above, is preferably methyl, in the presence of a molar excess of a mineral acid, for example, HCl, HBr, HI, and sulfuric acid, followed by treatment with a molar excess of base, for example, sodium bicarbonate or ammonia. In some embodiments it is preferred to carry out the solvolysis reaction at a temperature of from about −30° C. to about 25° C., more preferably the hydrolysis is carried out at a temperature of about −10° C. or less.

In some embodiments, it is preferred to carry out the cyanation reaction using potassium cyanide and the imine racamate prepared in step 3 suspended in from about 7 to about 10 volumes of methanol in the presence of from about 1.1 equivalents to about 2 equivalents of glacial acetic acid based on the amount of imine to be cyanated. In some embodiments, it is preferred to carry out the reaction at a temperature of from about −10° C. to about 0° C. In some embodiments wherein the cyanation reaction is carried out using the KCN/acetic acid process, it is preferred to carry out the solvolysis step (with reference to Scheme I, that is, Step 5) by cooling the methanolic reaction mixture after all of the substrate has been cyanated to a temperature of from about −20° C. to about −25° C. and to treat the cold reaction mixture with from about 3.2 to about 7 equivalents of HCl gas, based on the amount of cyanated substrate present. In some embodiments using this workup, it is preferred to bubble the required amount of HCl gas through the reaction mixture whilst maintaining the reaction mixture at a temperature about −10° C. or less.

In some embodiments using this workup, after the desired amount of HCl has been bubbled into the reaction mixture, the reaction mixture is warmed to room temperature to complete the methanolysis reaction, thus providing the racemate of formula VII. In some embodiments using this workup, it is preferred to carry out the completion of the methanolysis at an elevated temperature, for example, from about 50° C. to about 60° C. In some embodiments using this work up, after the methanolysis reaction is complete, it is preferred to concentrate the reaction mixture to a slurry, dilute the slurry with from about 4 volumes to about 8 volumes of MTBE and about 4 volumes of water, cool the mixture to a temperature of from about −5° C. to about +5° C., and add to the cold mixture about 0.2 equivalents of potassium phosphate tribasic dissolved in two additional volumes of water.

In some embodiments using this work up procedure it is preferred to adjust the pH with aqueous base to a pH of from about pH 9 to about pH 9.5 while maintaining the temperature of the mixture at from about 0° C. to about +5° C. In some embodiments using this work up, it is preferred to separate out the MTBE layer, wash it, and concentrate it to a volume of from about ½ to about ⅓ the volume, and replace the MTBE in the concentrate with methanol by distilling off the MTBE after the addition of methanol. In some embodiments using this work up, the resulting methanol solution containing the formula VII racemate is utilized in Step 6.

Step 6—Enantiomeric Salt Formation

With reference to Step 6 of Scheme I, the formation of a selected enantiomer salt is accomplished by adding to the racemate of formula VII either: (a) D-DTTA (di-p-toluoyl-D-tartaric acid) or D-DBTA (dibenzoyl-D-tartaric acid) to precipitate the (1R,2S,5S) enantiomer; or (b) L-DTTA (di-p-toluoyl-L-tartaric acid) or L-DBTA (dibenzoyl-L-tartaric acid) to precipitate the (1S,2R,5R) enantiomer shown. Each of these chiral acids is a commercially available reagent. As mentioned above, D-DTTA reacts with the (1R,2S,5S) enantiomer present in the racemate of formula VII and L-DTTA with the (1S,2R,5R) enantiomer present in the racemate of formula VII, precipitating the corresponding di-p-toluoyl-tartaric acid salt in at least about 90% enantiomeric excess. Similarly, D-DBTA reacts with the (1R,2S,5S) enantiomer present in the racemate of formula VI and L-DBTA with the (1S,2R,5R) enantiomer present in the racemate of formula VII, producing the corresponding dibenzoyl-tartaric acid salt in at least about 85% enantiomeric excess. In some embodiments, it is preferred to employ solvents in this step selected from methanol, TBME and mixtures thereof. When mixed solvents are used, it is preferred to use a ratio of TBME: MeOH of from about 2:1 to about 4:1. In some embodiments of the invention, it is preferred to carry out the precipitation reaction at a temperature of from about 15° C. and about 50° C.

In some embodiments of the present invention process, the enantiomer salt precipitated in Step 6, for example, the salt of formulae SI and SIa, for example, a DTTA salt of formula SI, is converted to an HCl salt in accordance with the following process, for subsequent use in the synthesis of HCV protease inhibitor compounds. In some embodiments, the isolated enantiomeric salt is suspended in a mixture of isopropyl alcohol and MTBE, preferably in a volumetric ratio of i-propanol: MTBE of from about 1:7 to about 1:8. This suspension is treated with from about 1.18 to about 1.20 equivalents of hydrochloric acid in an isopropanol solution (based on the amount of salt used), preferably having a concentration of 5M or less. In some embodiments using the optional HCl salt conversion step, when the conversion has proceeded to completion the reaction mixture is cooled to insure that the hydrochloride salt has precipitated. When precipitation has completed, the precipitate is isolated by filtration and vacuum dried.

The following non-limiting EXAMPLES are provided to illustrate further the present invention. It will be apparent to those skilled in the art that many modifications, variations and alterations to the present disclosure, both to materials, methods and reaction conditions, may be practiced. All such modifications, variations, and alterations are intended to be within the spirit and scope of the present invention.

EXAMPLES

Unless otherwise stated, all solvents and reagents are articles of commerce, and used as received. Unless otherwise stated, the following abbreviations have the stated meanings in the Examples below:

mL=milliliters
g=grams
eq=equivalents
THF=tetrahydrofuran
MeOH=methanol
Me=methyl
TBME=methyl tert-butyl ether
ACN=acetonitrile
Ph=phenyl Step 1: Preparation of
6,6-Dimethyl-3-aza-bicyclo[3.1.0]hexane-2,4-dione
(III)

Procedure A

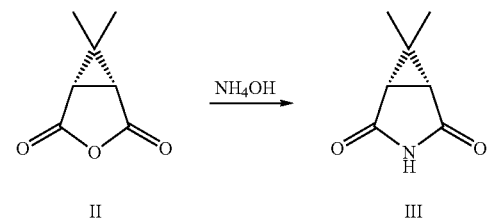

Example A1

To a flask was charged 300 g of II (2.1 mol, 1 eq.) and 300 mL of water. While stirring, the mixture was cooled to 0 to 10°

C. 225 mL of NH₄OH solution (14.8 M NH₃ in water) (3.3 mol, 1.5 eq.) were slowly added to the reaction mixture while stirring. During addition the reaction mixture temperature was maintained below 40° C. After the addition was complete, the batch was warmed to 105 to 115° C., and the water was collected by distillation while avoiding steam-distilling the product. Once the distillation was complete, the reaction mixture was heated gradually to between 165 to 180° C. to complete the cyclization. The reaction mixture was then cooled to a temperature between 60 to 70° C. and 200 mL of THF were added. The reaction mixture was reheated to 135 to 140° C. and the solvent was collected by distillation. The reaction mixture was recooled to a temperature between 60 and 70° C. and 200 mL of THF and 500 mL of n-heptane were added. The reaction mixture was cooled to 0 to 10° C. over a 5 hour period and then stirred for 0.5 to 1 hour, and the product was crystallized. The crystals were collected, washed, and dried to yield compound III as a white crystalline powder (yield 90-95%). ¹H NMR (CDCl₃) δ 7.55 (bs, 1H), 2.31 (d, J=1.12 Hz, 2H), 1.35 (s, 3H), 1.24 (s, 3H).

Example A2

Into a 12 L flask equipped with a temperature probe, distillation apparatus and mechanical stirrer was charged 1500.0 g of caronic anhydride (formula II, 10.7 mol). To the flask was added 1500 mL water followed by dropwise addition of NH₄OH (273.4 g, 16.1 mol). Water was collected by distillation at atmospheric for 2 hours. The mixture was then heated to 155° C. and stirred an additional 22 hours. Analysis by ¹H NMR and HPLC indicated incomplete conversion to product. To the mixture was then added additional NH₄OH (50.4 g, 3.0 mol). The mixture was heated to 155° C. for 1 hour. The reaction mixture was cooled to 120° C. and 7500 mL of normal butylacetate (n-BuOAc) was charged dropwise to the flask. The mixture was heated and maintained at a temperature of between 120° C.-130° C. n-BuOAc (6000 mL) and water (200 mL) were collected by distillation at atmosphere. The mixture was then cooled to 100° C. and n-heptane (6000 mL) was added dropwise, maintaining the internal temperature between 90 and 98° C. The reaction mixture was cooled to room temperature overnight. The white suspension was filtered and the cake washed with n-heptane (4500 mL). The wet product was dried in a vacuum oven at 40° C. to give the aza-dione compound of formula III (1413.3 g, 95%) as an off-white solid.

Example A3

Scheme III

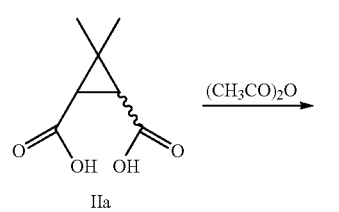
IIa

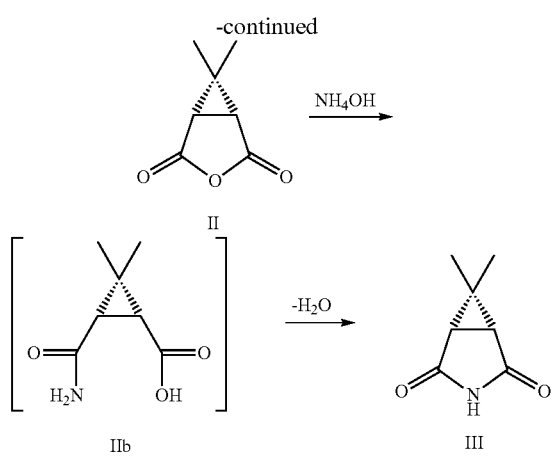

Preparation of Imide III from 3,3 dimethyl-cyclopropane-1,2-dicarboxylic acid (IIa) via Caronic anhydride II was carried out by slurrying 50 grams of cis/trans-3,3-dimethyl-1,2-cyclopropane dicarboxylic acid (IIa) in toluene (75 ml) and adding acetic anhydride (60 mL). After that conc. sulfuric acid (0.5 mL) was charged, and the toluene was slowly distilled off. The reaction mixture was heated to about 190° C. while the remaining volatile compounds were collected by distillation. The reaction was cooled below 50° C. and THF (50 mL) was added. After cooling to about 0° C., ammonium hydroxide (32 mL, about 14.8N) was slowly charged while maintaining the temperature below 15° C. The mixture was then slowly heated to 110° C. while distilling off the THF. The reaction was further heated in stages to 180° C. After cooling and addition of THF (15 mL) the reaction was reheated to 140° C. while collecting the solvent by distillation. The mixture was cooled and THF (15 mL) and n-heptane (30 mL) were added. Distillation of solvent followed by cooling gave the crystalline imide 111 (Yield: 85%).

Procedure B

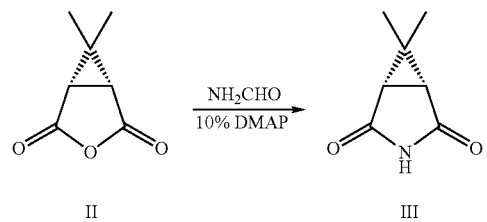

Into a three-necked, round bottom flask equipped with a temperature probe, condenser, and mechanical stirrer was placed 25.0 g of the compound of formula II (caronic anhydride). To the flask was added 9.37 mL of formamide (10.61 g, 0.424 equivalents based on anhydride) followed by 2.43 g of 4-N,N-dimethyl aminopyridine (DMAP, 0.1 equivalents). The vessel was purged with nitrogen and the reaction mixture heated to 145° C. with agitation, heating was continued for 2.5 hours. After proton NMR measurements indicated that the anhydride was completely consumed, the solution was cooled to 90° C. and the vessel was charged with 50 ml of xylenes (2 volumes).

The reaction mixture was then heated to 145° C. with agitation. Heating was continued for 2.5 hours while operating the Dean-Stark condenser collecting a water/formamide azeotrope. After removal of excess formamide from the reaction mixture and conversion of all intermediates, the reaction mixture was cooled to 80° C. The reaction flask was then charged with 18.75 ml of heptanes (0.75 volumes) and the reaction mixture temperature was maintained at 80° C. After the addition of heptanes was complete, the reaction mixture was cooled over 2 hours to 0° C. and maintained in at a temperature of from 0° C. to 5° C. for 30 minutes with agitation. At the end of the reaction mixture was maintained in this temperature range with agitation for 30 minutes during which time a precipitate formed. The solids were collected by filtration and washed with two 50 mL aliquots of cold heptanes, and dried in a vacuum oven for 24 hours at 50° C.

Procedure C

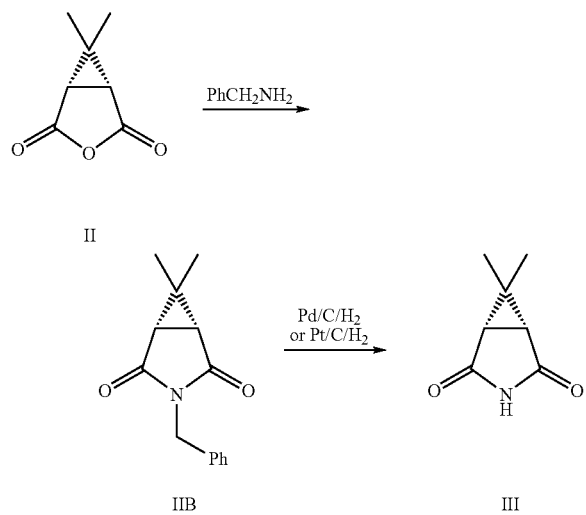

To a flask were charged 51.32 g of II (0.37 mol, 1 eq) and 50 mL TBME. While stirring, the mixture was cooled to between 0 and 10° C. 40.0 mL of benzylamine (39.24 g, 0.37 mol, 1 eq) was added dropwise over approximately 30 minutes. After the addition was complete, the TBME was removed by distillation at between 60 and 70° C., and the mixture was gradually heated to an internal temperature between 170 and 180° C. The solution was maintained between 170 and 180° C. for approximately 3 to 5 hours to complete the cyclization. The resulting solution was cooled to between 60 and 70° C., and 100 mL of a solution of 5% water in isopropanol was added, and the mixture was cooled to room temperature. After cooling further to between 0 and 10° C., the product was isolated by filtration, rinsed with clean, cold isopropanol, and dried in a vacuum oven to afford 70.99 g of the benzyl imide, IIB, (85%). $^1$H NMR (CDCl$_3$) δ 7.39 (m, 2H); 7.28 (m, 3H); 4.53 (s, 2H); 2.31 (s, 2H); 1.20 (s, 3H); 1.01 (s, 3H). This product can be deprotected using conventional hydrogenolysis conditions (H$_2$, Pd/C) to afford III.

Step 2: Preparation of
6,6-Dimethyl-3-aza-bicyclo[3.1.0]hexane (IV)

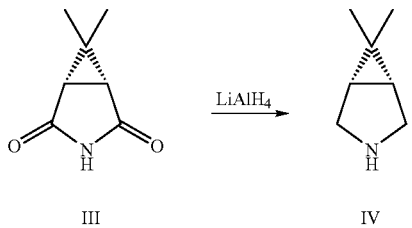

A THF solution of LiAlH$_4$ (500 mL, 2.4 M, 1.2 mol, 1.67 eq.) was charged into a 3-neck flask fitted with an N$_2$ inlet. The contents of the flask were warmed to 40° C. while being purged with nitrogen. 100 g of III (0.72 mol, 1 eq.) and 400 mL of THF were added to a second flask and stirred until a clear solution was formed. The solution containing III in the second 3-necked flask containing was then added over an approximately 0.5 to 1 hour period to the reaction mixture containing LiAlH$_4$ in the first 3-neck flask while allowing the temperature to rise to approximately 70° C. (reflux). The second flask was rinsed with 100 mL of THF, which was added to the reaction mixture to ensure complete transfer of III. Upon completion of the addition of the solution, the reaction mixture was maintained at reflux temperature and stirred until the reaction was complete (approximately 3 hours).

To a 3-necked flask fitted with a nitrogen inlet were charged 674 g of potassium sodium tartrate tetrahydrate (2.39 mol, 3.32 eq) and 191 g of sodium hydroxide (4.78 mol, 6.64 eq), 800 mL of H$_2$O and 300 mL TBME. The mixture was agitated between 15 and 25° C. for approximately 1 hour, or until all of the solids had dissolved. The reaction mixture was transferred via cannula to the biphasic quench mixture over approximately 10 to 20 minutes. The reaction flask was rinsed with 30 mL TBME which was also transferred via cannula to the quench flask. The biphasic mixture was agitated for an additional 15 to 30 minutes, and the layers were split at 40° C. The aqueous layer was extracted twice with 100 mL TBME. The combined organic layers were fractionally distilled to yield IV as a colorless liquid (64.5 g, 88%). $^1$H NMR (CDCl$_3$, 400 MHz): δ 3.07 (m, 2H), 2.89 (d, 2H, J=11.6 Hz), 1.56 (br s, 1H), 1.25 (m, 2H), 1.00 (s, 3H), 0.98 (s, 3H).

Alternatively, compound IV in TBME solution from above was converted to its corresponding hydrochloric acid salt. First, the TBME was removed by distillation. Second, a 18.6 g aliquot of the concentrated solution containing compound IV was taken and charged to a 500 mL, 3-neck flask equipped with mechanical stirrer, an N$_2$ line, a glass tube fixed through a 24-40 septa and an adapter to a 3N NaOH bubbler. The solution was cooled to −20° C. and held between −20 and −23° C. and gaseous HCl was bubbled through the solution while stirring for 10 minutes. A white precipitate was immediately apparent. The reaction was monitored by NMR and additional gaseous HCl was bubbled if necessary. The precipitate was filtered under a blanket of N$_2$ and washed with chilled heptanes (−60° C., 40 mL) under N$_2$ to give, after drying, 13.9 g, (70%) the IV*HCl salt. $^1$H NMR (CDCl$_3$, 400 MHz): δ 7.90 (BS, 1H), 3.55 (d, J=16.4, 2H), 3.15 (d, J=16.4, 2H), 1.60 (m, 2H), 1.10 (s, 3H), 1.02 (s, 3H).

Step 3: Preparation of
6,6-dimethyl-3-aza-bicyclo[3.1.0]hex-2-ene (V)

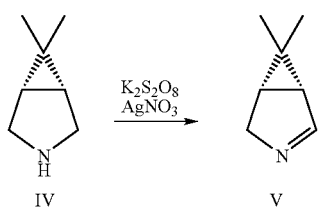

To a flask were charged 41.4 g of NaOH (1.04 mol, 2.3 eq.) and 134 g of K$_2$S$_2$O$_8$, 750 mL of water and 100 mL of acetonitrile at −5° C. 50 g of IV (0.45 mol, 1.0 eq) were added, and the reaction mixture was again cooled to −5° C. Over 1-2 hours while maintaining the reaction temperature between −5 and 0° C., 20 mL of aqueous AgNO$_3$ (3.9 g, 0.0225 mol, 0.05 eq) were added to the reaction mixture. The reaction mixture was warmed to 0 to 2° C., and the reaction was allowed to proceed to completion. Upon completion, the mixture was warmed to room temperature and diluted with 360 mL TBME. The layers were separated, and the aqueous layer was extracted with TBME. The combined organic layers were dried over anhydrous Na$_2$SO$_4$ and filtered. The solution was purified by fractional distillation to yield V as a colorless oil which solidified upon standing to form a white crystalline solid V, (65-75% yield). $^1$H NMR (CDCl$_3$) δ 7.30 (t, J=2.2 Hz, 1H), 3.80 (ddd, J=6.8, 1.4, 0.6 Hz, 1H), 3.49 (dd, J=4.7, 2.8 Hz, 1H), 2.06 (dd, J=6.0, 1.7 Hz, 1H), 1.61 (dd, J=6.6, 1.8 Hz, 1H), 1.03 (s, 3H), 0.68 (s, 3H).

Step 4 and 5: Preparation of methyl 6,6-dimethyl-3-azabicyclo[3.1.0]hexane-2(RS)-carboxylate (VIIA) Via the Corresponding Cyano-Compound (VI)

Example 4a

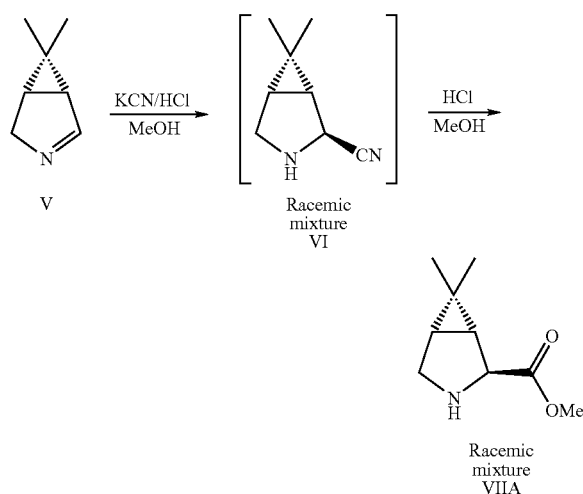

To a flask were charged 47 g of imine V (0.43 mol, 1.0 eq), 350 mL of methanol and 30.9 g KCN (0.47 mol, 1.1 eq). The mixture was cooled to −5° C., and 85.0 ml of HCl (0.2 g/ml in MeOH) (0.46 mol, 1.1 eq) were added dropwise while keeping the temperature between −5 to −2° C. The mixture was stirred until the reaction was complete. The reaction mixture was then cooled to −20 to −30° C., and 64.5 g of gaseous HCl (1.77 mol, 4.1 eq) were bubbled slowly into the reaction mixture while maintaining the reaction temperature. After the addition was complete, the reaction mixture was slowly warmed-up to room temperature. VI, $^1$H NMR (CDCl$_3$) δ 3.93 (d, J=4.0 Hz, 1H), 3.30 (dt, J=10.9, 5.4 Hz, 1H), 1.02 (s, 3H), 2.99 (dd, J=10.6, 3.5 Hz, 1H), 1.83 (s, 1H), 1.56 (d, J=7.1 Hz, 1H), 1.48 (dd, J=7.3, 5.0 Hz, 1H), 1.03 (s, 3H).

The reaction mixture was then cooled to −20 to −30° C. and 29.0 g of gaseous ammonia (1.81 mol, 4.2 eq) were bubbled slowly in to the reaction mixture while maintaining the reaction temperature until the pH was 10. The reaction mixture was warmed up to −10° C., filtered, and the filter cake was washed with TBME. The filtrate was concentrated, and the residue was extracted with water and TBME. After layer separation, the TBME solution was dried over MgSO$_4$, filtered, and concentrated under reduced pressure to give 58 g of VIIA (82% yield). $^1$H NMR (CDCl$_3$) δ 3.67 (s, 3H), 3.59 (s, 1H), 3.3 (dd, J=10.2, 5.1 Hz, 1H), 2.88 (d, J=10.2 Hz, 1H), 1.98 (s, 1H), 1.41 (d, J=7.1 Hz, 1H), 1.25 (dd, J=7.1, 5.1 Hz, 1H), 1.04 (s, 3H), 0.95 (s, 3H).

Example 4b

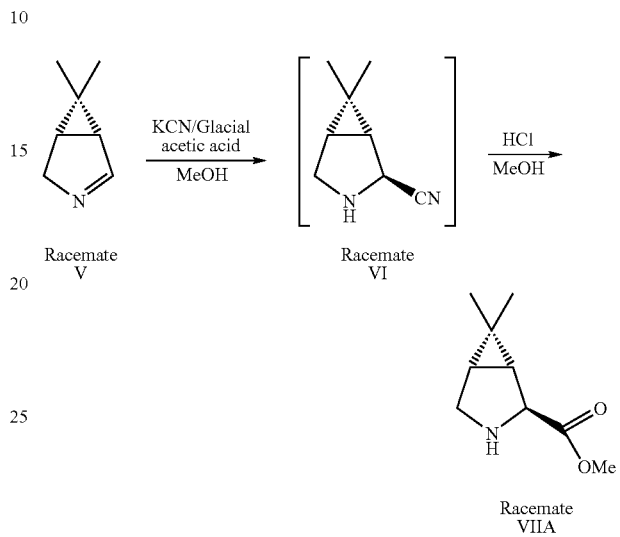

Into a flask was placed 329 ml of methanol, 47 g of the imine racemic mixture of formula V previously prepared, and 30.9 g of KCN (1.1 equivalents). The mixture was stirred and cooled to a temperature of −10° C. To the cooled mixture, with continued stirring was added 28.4 g of glacial acetic acid (1.1 equivalents) over a period of about 30 minutes while maintaining the temperature. After the acetic acid addition, the mixture was stirred for several minutes while maintaining the temperature. When all of the imine had been converted to a cyano adduct (racemate of formula VI), the temperature of the reaction mixture was lowered to about −25° C. and 66 g of HCl gas was bubbled into the reaction mixture. During sparging with HCl gas, the temperature of the reaction mixture was maintained below −10° C. After the entire amount of HCl had been bubbled into the mixture, the mixture was warmed to room temperature and agitated for an additional 16 hours to complete the hydrolysis of the cyano compound, thereby providing the racemate of formula VII.

After hydrolysis had completed, the reaction mixture was concentrated to a volume of 117 ml. Following concentration, 376 ml of MTBE and 188 ml of water were added. The mixture was cooled to −5° C., and an aqueous solution containing 18.3 g K$_3$PO$_4$ in 94 ml H$_2$O was added with stirring while maintaining the temperature. The pH of the mixture was adjusted to a pH of 9.5 by adding 63.3 ml of 25% aqueous NaOH solution. During this process, the temperature of the reaction mixture was maintained at a temperature of from −5° C. to 0° C. The organic and aqueous layers of the reaction mixture were separated. The aqueous layer was extracted with 235 ml MTBE. The MTBE extract was combined with the organic layer, the combined organics were washed with 5 aliquots of brine solution. The resulting organic solution was employed in the next step of the inventive process. An aliquot of the solution was analyzed by GC which indicated that the racemic azabicyclo-carboxylate of formula VIIIa was provided in a yield of 82% based on the amount of imine of formula V employed.

Step 6: Preparation of methyl 6,6-dimethyl-3-azabicyclo[3.1.0]hexane-(2S)-carboxylate D-DTTA Salt (IB)

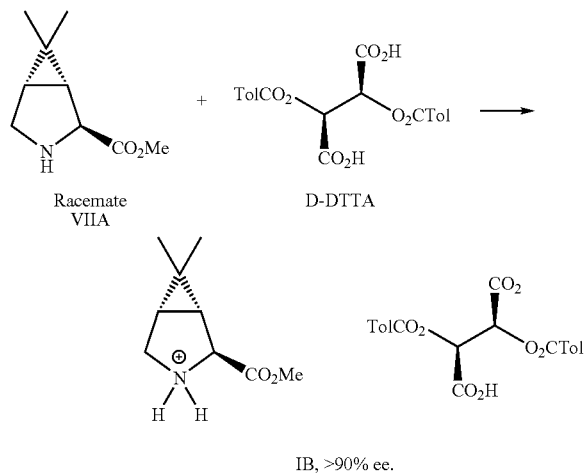

To a flask were charged 4.2 g of D-DTTA (10. mmoles) and 22 mL of methanol at room temperature. The reaction mixture was stirred until dissolved. Next, 4.2 g of 3.7 g (21.9 mmoles) of VIIA in 41 ml of TBME was added over a 10 minute period, and the reaction mixture was stirred for 30 minute or until salt started to form. The reaction mixture was then warmed to 40-50° C. and held at that temperature for 1 hour. The mixture was then cooled to a temperature between 15-25° C. over a 20 minute period and stirred for 1 hour. The suspension was filtered, and the filter cake was washed TBME (15 ml). The cake was dried at a temperature of 40-50° C. to give a typical yield of 4.86-5.0 g (40-42%) of IB with a 95-97% e.e. $^1$H NMR (400 MHz, CDCl$_3$) δ 7.92 (d, J=8.2 Hz, 4H), 7.16 (d, J=8.1 Hz, 4H), 7.05 (broad s, 3H), 5.70 (s, 2H), 4.21 (d, J=1.0 Hz, 1H), 3.74 (s, 3H), 3.68 (dd, J=12.4, 6.2 Hz, 1H), 3.30-3.27 (m, 1H), 2.36 (s, 6H), 1.66-1.64 (m, 1H), 1.53-1.49 (m, 1H), 0.97 (s, 6H).

Optional Conversion Step: Converting 6,6-dimethyl-3-azabicyclo[3.1.0]hexane-(2S)-carboxylate D-DTTA Salt (IB) to the Corresponding Hydrochloride Salt

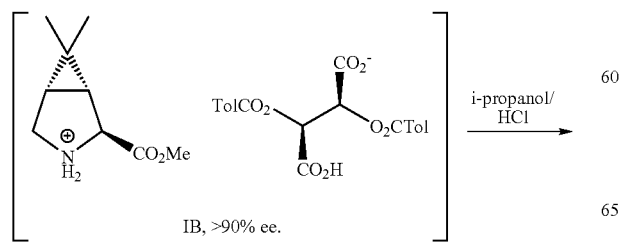

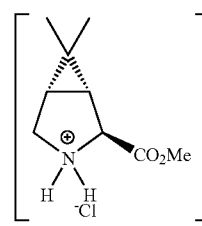

Into a 3-neck, half-jacketed flask fitted with an overhead stirrer, funnel, and addition funnel was placed 200.13 g (360.2 mmol) of the DTTA salt prepared in Step 6. Through the funnel, under ambient conditions was added 60 ml of isopropanol (2.18 equivalents based on the amount of salt added), and 450 ml (10.49 equivalents) of t-butyl methyl ether (MTBE). The funnel was removed and the flask was sealed with a temperature probe in its place. Via the addition funnel, with stirring, under ambient conditions, 87 ml of 4.97 M i-propanol/HCl (1.20 equivalents) was added to the reaction mixture over a 15 minute period. Stirring was continued for 5 minutes after the HCl addition had completed and an additional 670 mL of MTBE was added via the addition funnel over the next 2.5 hours with continued stirring under ambient conditions. After completion of the additional MTBE, stirring was continued for 1.25 hours under ambient conditions. At the end of this period, the reaction mixture was cooled to 10.0° C. and held quiescent for 30 minutes. The resulting precipitate was collected in a Buchner funnel, and washed with aliquots of the following solvents (each aliquot was cooled to a temperature of 4° C. prior to washing the filtrate): two aliquots of 150 mL MTBE in sequence followed by one 120 mL aliquot of MTBE. The resultant white solid was dried at room temperature in a vacuum oven (23.5 mm Hg) for three days whilst a nitrogen purge was passed through the vacuum oven. The weight of the dried product indicated an uncorrected yield of 66.27 g (89.4% yield based on the amount of starting salt used).

While the present invention has been described with and in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula:

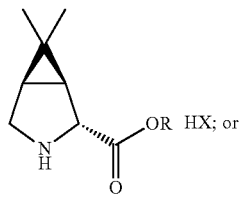

of the formula:
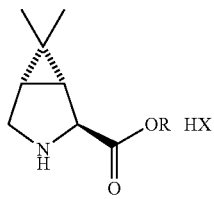
wherein
R represents an alkyl, substituted alkyl, aryl, substituted aryl, aralkyl substituted aralkyl, cycloalkyl, or substituted cycloalkyl group; and
X is D-DTTA, L-DTTA, D-DBTA or L-DBTA.
2. The compound according to claim 1, wherein R is $C_1$-$C_8$ alkyl.
3. The compound according to claim 1, wherein R is methyl.
* * * * *